United States Patent
Kaese et al.

(12)

(10) Patent No.: US 6,854,172 B2
(45) Date of Patent: Feb. 15, 2005

(54) PROCESS FOR PRODUCING BIORESORBABLE IMPLANTS

(75) Inventors: Volker Kaese, Hannover (DE); Arne Pinkvos, Langenhagen (DE); Heinz Haferkamp, Garbsen (DE); Matthias Niemeyer, Hannover (DE); Friedrich-Wilhelm Bach, Isernhagen (DE)

(73) Assignee: Universitaet Hannover, Hannover (DE)

( * ) Notice: Subject to any disclaimer, the term of this patent is extended or adjusted under 35 U.S.C. 154(b) by 117 days.

(21) Appl. No.: 10/369,138

(22) Filed: Feb. 20, 2003

(65) Prior Publication Data

US 2003/0221307 A1 Dec. 4, 2003

(30) Foreign Application Priority Data

Feb. 20, 2002 (DE) ......................................... 102 07 161

(51) Int. Cl.$^7$ ............................................... B23P 25/00
(52) U.S. Cl. ........................ 29/412; 29/417; 29/527.6; 29/557; 623/1.13; 623/1.15; 623/23.7; 623/23.71; 623/901; 623/924; 428/577; 428/398; 148/538; 148/557; 148/705; 148/406
(58) Field of Search ...................... 29/412, 417, 527.5, 29/527.6, 33 C, 26 A, DIG. 26, DIG. 49, DIG. 50; 148/537, 557, 666, 667, 705, 406, 420, 441; 164/69.1, 262; 428/577, 398; 623/1.13, 1.15, 20.14, 23.7, 23.71, 901, 924

(56) References Cited

U.S. PATENT DOCUMENTS

| 4,714,468 | A | * | 12/1987 | Wang et al. ................. 424/423 |
| 5,509,933 | A | * | 4/1996 | Davidson et al. ......... 623/23.53 |
| 5,693,158 | A | * | 12/1997 | Yamamoto et al. ......... 148/557 |
| 6,013,854 | A | * | 1/2000 | Moriuchi .................... 623/1.11 |
| 6,131,266 | A | * | 10/2000 | Saunders ...................... 29/557 |
| 6,287,332 | B1 | | 9/2001 | Bolz et al. |
| 2002/0004060 | A1 | | 1/2002 | Heublein et al. |

FOREIGN PATENT DOCUMENTS

| DE | 197 31 021 | | 7/1997 | |
| EP | 709 067 | | 5/1996 | |
| EP | 966 979 | | 6/1999 | |
| FR | 2753080 A1 | * | 3/1998 | ............. A61F/2/02 |
| WO | WO 95/17530 | | 6/1995 | |
| WO | WO0060131 A2 | * | 10/2000 | |

* cited by examiner

Primary Examiner—Essama Omgba
Assistant Examiner—Jermie E. Cozart
(74) Attorney, Agent, or Firm—Crowell & Moring LLP

(57) ABSTRACT

A process for producing implants made of a bioresorbable metal, particularly magnesium alloys or zinc alloys, in which the material properties of the magnesium or the zinc are changed and the processing and utilization properties are improved by combining process steps for adjusting the properties of the material and subsequent machining. In this way it is possible to produce thin-walled tubular implants, particularly blood vessel support stents, from bioresorbable magnesium or zinc alloys, which are readily deformable without the risk of fracture during implantation.

17 Claims, No Drawings

PROCESS FOR PRODUCING BIORESORBABLE IMPLANTS

CROSS REFERENCE TO RELATED APPLICATION

This application claims priority from Federal Republic of Germany patent application no. DE 102 07 161.6, filed Feb. 20, 2002, the entire disclosure of which is incorporated herein by reference.

BACKGROUND OF THE INVENTION

The invention relates to a process for the production of implants made of bioresorbable metal, particularly magnesium alloys or zinc alloys.

Processes for the production of bioresorbable metal implants of the initially described type are known in practice through prior public use and thus form part of the prior art. These processes are used, for instance, to produce screws or pins made of magnesium alloys for the fixation of fractured bones.

Implants made of bioresorbable metal are distinguished in that they corrode in the human body and dissolve almost without residue. The time span within which these implants dissolve completely can be adjusted by means of the type or the amount of the alloy components used. As a result, the pins or screws, which are superfluous once the fractures have healed, no longer need to be surgically removed. This eases the patient's healing process enormously. It also makes the physician's work easier and saves time, and thereby reduces health care costs significantly.

However, the material properties, e.g., the hexagonal lattice structure and the associated low ductility at room temperature limit the processing of these bioresorbable metals. In particular, the use of such implants is restricted to applications where possible fragments cannot get into the patient's bloodstream. This restricts the possible uses of magnesium or zinc alloys essentially to implants for bone fractures.

SUMMARY OF THE INVENTION

Accordingly, it is an object of the invention to provide an improved process for producing implants of bioresorbable metals.

Another object of the invention is to provide a process for producing implants that will expand the possible uses of bioresorbable metals, e.g., magnesium alloys or zinc alloys, for the production of implants.

These and other objects are achieved in accordance with the present invention by providing a process for producing an implant made of a bioresorbable metal, the process comprising the steps of producing a pin-shaped, semi-finished product from the bioresorbable metal by casting, heat treatment, and subsequent thermomechanical processing; cutting the semi-finished product in a longitudinal direction into at least two sections, and machining a respective section by a chip removing machining operation to produce a tubular implant.

Further improvements and preferred embodiments of the invention are described in detail hereinafter.

DESCRIPTION OF PREFERRED EMBODIMENTS

The invention provides a process in which a pin-shaped semi-finished product is produced from the bioresorbable metal through a casting process and a heat treatment, particularly homogenization, and a subsequent thermomechanical treatment, particularly extrusion. In a cutting process, this semi-finished pin is then cut into at least two sections in longitudinal direction. The respective section is then machined by chip removal to produce a tubular implant, particularly a vessel support device. This changes the material properties of the magnesium or the zinc and thereby improves the processing and utilization properties, so that the breaking off of fragments can be largely excluded.

By combining the upstream processes for adjusting the properties of the material and subsequent machining it is possible to produce thin-walled tubular implants, e.g., cardiovascular supports, from magnesium or zinc alloys. These tubular implants, so-called stents, support vessels, e.g., arteries, in the human body from the inside. This process assures that the tubular implants have sufficient mechanical strength and at the same time undergo uniformly controllable corrosion over the entire wall cross section.

The resulting implants produced in this way are deformable without the risk of fracture under load. This prevents possible injuries of the arteries by breaking implants or by implant fragments that have broken off and have been carried away as well as any undesired shifting of the entire implant.

Through casting and heat treatment, the magnesium or zinc and the corresponding alloy components are uniformly distributed. Any voids created during casting as well as any precipitations and impurities can be removed in an intermediate step by turning. This assures that the tubular implant dissolves uniformly and controllably over the entire wall cross section.

With the subsequent thermomechanical treatment, e.g., hot extrusion, the grain is reduced in size as a result of a high degree of deformation. This imparts the required mechanical strength to the pin-shaped semi-finished product, since a plurality of grains provide the mechanical support across the wall cross section.

In the first two process steps, uniform material properties are adjusted over the entire length of the pin-shaped semi-finished product. With extrusion, areas with different material properties are created over the cross section of the pin-shaped semi-finished product, because in extrusion deformation is greater in the external areas than in the internal area. For this reason, the pin-shaped semi-finished product is subsequently cut into at least two sections along its longitudinal axis. This makes it possible for the subsequent chip removing machining step to take sections from the areas with a high degree of deformation and thus with a high degree of reduction in grain size. The inside and outside diameters of the tubular implants are then produced by chip removing machining.

It is particularly advantageous if the pin-shaped semi-finished product is cut into three or four sections. This makes it possible to clamp these sections into a three- or four-jaw chuck for the chip removing machining step.

A particularly advantageous further development of the process is achieved if the machining by chip removal is carried out without the use of a cooling lubricant. Dry operation prevents corrosion along the walls that are created by chip removing machining. For dry operation, the tools must be sufficiently sharp.

A particularly advantageous embodiment of the invention is attained if the process steps are automated. This avoids delays in the production process as well as possible sources of error due to manual intervention. The result is an economically efficient process for producing tubular implants.

It is especially simple if the inside diameter of the tubular implant is produced by drilling and the outside diameter is produced by turning. To this end, the respective section is center drilled with a predefined desired inside diameter and the outer surface of the corresponding section is turned on the lathe to obtain the desired outside diameter.

Another particularly advantageous further development of the process is achieved if the inside diameter and the outside diameter of the tubular implant are produced simultaneously by chip removing machining. This makes it possible to obtain implants with particularly uniform thin walls having inside diameters of approximately 1.8 mm and outside diameters of approximately 2.0 mm with a length of approximately 15.0 mm. These uniform walls are especially important in radially deformable implants to obtain uniform loading and consequent deformation.

Another particularly advantageous modification of the process is achieved if fine machining is used after machining by chip removal. This prevents mechanically detrimental impairments of the surface quality of the tubular implant, e.g., due to nicks.

Yet another particularly advantageous embodiment of the process is achieved by using an athermal cutting process. This prevents changes in the microstructure and any diffusing out of low melting elements and alloy components in the pin-shaped semi-finished product, or in the respective sections, due to the heat that would otherwise be created or supplied in the cutting process.

It has proven to be particularly practical if a jet cutting process is used. This process does not produce any heat, so that microstructural changes are avoided. At the same time fine structures can be produced in this way with high precision.

A further particularly simple modification is achieved by using a saw blade with set teeth in the cutting process. This reduces heat development. The saw blade may furthermore be cooled.

Another particularly advantageous further development is achieved by carrying out a heat treatment, particularly ageing, after cutting of the semi-finished product. This makes it possible specifically to modify the mechanical property profile in a targeted manner.

Another particularly advantageous embodiment of the process is achieved if the pin-shaped semi-finished product is cut in such a way that when the tubular implant is produced, a central area encompassing the center axis of the pin-shaped semi-finished product is cut out. This prevents the so-called zero-core of the pin-shaped semi-finished product from being a component of the tubular implant. The zero-core is the region with the lowest degree of deformation and thus the lowest degree of grain size reduction.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A process for producing an implant made of a bioresorbable metal, said process comprising the steps of:
   producing a pin-shaped, semi-finished product from the bioresorbable metal by casting, heat treatment, and subsequent thermomechanical processing;
   cutting the semi-finished product in a longitudinal direction into at least two sections, and
   machining a respective section by a chip removing machining operation to produce a tubular implant.

2. A process according to claim 1, wherein said bioresorbable metal is a magnesium alloy or a zinc alloy.

3. A process according to claim 1, wherein said heat treatment is a homogenizing treatment.

4. A process according to claim 1, wherein said thermomechanical processing is effected by extrusion.

5. A process according to claim 1, wherein said tubular implant is a blood vessel support device.

6. A process according to claim 1, wherein the pin-shaped semi-finished product is cut into three or four sections.

7. A process according to claim 1, wherein the chip removing machining operation is performed without use of cooling lubricants.

8. A process according to claim 1, wherein the process steps are automated.

9. A process according to claim 1, wherein said tubular implant has an inside diameter produced by drilling and an outside diameter produced by turning.

10. A process according to claim 1, wherein the tubular implant is simultaneously machined by chip removal inside to produce the inside diameter and outside to produce the outside diameter.

11. A process according to claim 1, wherein after the chip removing machining, the tubular implant is subjected to fine machining.

12. A process according to claim 1, wherein the cutting is carried out by an athermal cutting process.

13. A process according to claim 1, wherein the cutting is carried out by a jet cutting process.

14. A process according to claim 1, wherein the cutting is carried out by a saw blade with set teeth.

15. A process according to claim 1, further comprising subjecting the cut sections of the semi-finished product to a further heat treatment prior to machining.

16. A process according to claim 15, wherein said further heat treatment is an ageing process.

17. A process according to claim 1, wherein the pin-shaped semi-finished product is cut in such a way that when the tubular implant is produced, a central area encompassing the center axis of the pin-shaped semi-finished product is cut out.

* * * * *